(12) United States Patent
Sargeant et al.

(10) Patent No.: US 8,968,760 B2
(45) Date of Patent: Mar. 3, 2015

(54) ATTACHMENT OF A BIOMATERIAL TO TISSUE

(75) Inventors: Timothy Sargeant, Guilford, CT (US); Jonathan Thomas, New Haven, CT (US)

(73) Assignee: Covidien LP, Mansfield, MA (US)

( * ) Notice: Subject to any disclaimer, the term of this patent is extended or adjusted under 35 U.S.C. 154(b) by 338 days.

(21) Appl. No.: 13/404,242

(22) Filed: Feb. 24, 2012

(65) Prior Publication Data

US 2012/0277773 A1 Nov. 1, 2012

Related U.S. Application Data

(60) Provisional application No. 61/479,565, filed on Apr. 27, 2011.

(51) Int. Cl.
- *A61F 2/02* (2006.01)
- *A61B 17/88* (2006.01)
- *A61B 17/00* (2006.01)
- *A61L 31/04* (2006.01)
- *A61K 38/00* (2006.01)

(52) U.S. Cl.
CPC ........... *A61B 17/00491* (2013.01); *A61L 31/04* (2013.01)
USPC ..... 424/422; 424/423; 424/9.341; 424/9.351; 424/1.13; 424/1.73; 427/2.14; 427/2.24; 427/427.4; 427/446; 427/447; 523/113; 523/115

(58) Field of Classification Search
CPC .................................................. C08L 2203/02
See application file for complete search history.

(56) References Cited

U.S. PATENT DOCUMENTS

| | | | |
|---|---|---|---|
| 5,306,500 A | 4/1994 | Rhee et al. | |
| 5,919,551 A * | 7/1999 | Cobb et al. | 428/156 |
| 6,391,060 B1 | 5/2002 | Ory et al. | |
| 6,408,656 B1 | 6/2002 | Ory et al. | |
| 6,443,964 B1 | 9/2002 | Ory et al. | |
| 6,451,032 B1 | 9/2002 | Ory et al. | |
| 6,478,737 B2 | 11/2002 | Bardy | |
| 6,514,534 B1 | 2/2003 | Sawhney | |
| 6,566,406 B1 | 5/2003 | Pathak et al. | |
| 6,605,294 B2 | 8/2003 | Sawhney | |
| 6,695,855 B1 | 2/2004 | Gaston | |
| 6,703,047 B2 | 3/2004 | Sawhney et al. | |
| 6,818,018 B1 | 11/2004 | Sawhney | |
| 6,971,252 B2 | 12/2005 | Therin et al. | |
| 7,009,034 B2 | 3/2006 | Pathak et al. | |
| 7,021,086 B2 | 4/2006 | Ory et al. | |
| 7,332,566 B2 | 2/2008 | Pathak et al. | |
| 7,347,850 B2 | 3/2008 | Sawhney | |
| 7,596,002 B2 | 9/2009 | Teichmann | |
| 8,043,631 B2 * | 10/2011 | Au et al. | 424/468 |
| 2003/0108511 A1 | 6/2003 | Sawhney | |
| 2005/0043814 A1 | 2/2005 | Kusanagi et al. | |
| 2007/0009709 A1 * | 1/2007 | Krishnan et al. | 428/141 |
| 2007/0032805 A1 | 2/2007 | Therin et al. | |
| 2008/0114092 A1 | 5/2008 | Sawhney | |
| 2010/0009712 A1 * | 1/2010 | Kodama | 455/550.1 |
| 2011/0224323 A1 * | 9/2011 | Bigwood et al. | 521/182 |
| 2011/0282464 A1 * | 11/2011 | Sargeant et al. | 623/23.58 |

FOREIGN PATENT DOCUMENTS

| | | |
|---|---|---|
| EP | 2 143 737 A1 | 1/2010 |
| EP | 2 196 193 A1 | 6/2010 |
| EP | 2 233 160 A2 | 9/2010 |
| EP | 2 233 161 A2 | 9/2010 |

OTHER PUBLICATIONS

International Search Report issued in Application EP 11250562.3 mailed Dec. 8, 2011.
International Search Report issued in Application EP 11250564.9 mailed Dec. 8, 2011.
International Search Report issued in Application EP 11250563.1 mailed Dec. 27, 2011.
International Search Report issued in Application EP 11250566.4 mailed Dec. 22, 2011.
International Search Report issued in Application EP 11250565.6 mailed Dec. 23, 2011.
International Search Report from application EP 10251719.0 mailed May 24, 2013.

* cited by examiner

*Primary Examiner* — Maryam Monshipouri
*Assistant Examiner* — Samuel Liu

(57) ABSTRACT

A method for attaching an implant to tissue is disclosed. In embodiments, a method includes applying a sprayable material to tissue, the sprayable material possessing functional groups capable of binding to tissue. The sprayable material also possesses functional groups capable of binding to an implant. In embodiments, the functional groups capable of binding to an implant include nucleotides. In such a case, the implant possesses complementary nucleotides capable of binding to the nucleotides on the sprayable material, thereby permitting hydrogen binding between the two. The implant may thus be affixed to tissue, and repositioned as necessary, prior to more permanent attachment utilizing means such as sutures, tacks, etc.

18 Claims, 1 Drawing Sheet

ATTACHMENT OF A BIOMATERIAL TO TISSUE

CROSS-REFERENCE TO RELATED APPLICATIONS

This application claims the benefit of, and priority to, U.S. Provisional Patent Application Ser. No. 61/479,565 filed on Apr. 27, 2011, the disclosure of which is hereby incorporated by reference in its entirety.

TECHNICAL FIELD

The present disclosure relates to the attachment of implants, in embodiments meshes, films and similar biomaterials, to tissue. More particularly, the present disclosure relates to the use of a sprayable material that facilitates attachment of an implant to tissue.

BACKGROUND

Techniques for repairing damaged or diseased tissue are widespread in medicine. Wound closure devices, such as sutures and staples, as well as other repair devices like mesh or patch reinforcements, are frequently used for repair. Various means have been utilized to attach these meshes to tissue, including staples, tacks, sutures, combinations thereof, and the like.

There has been a trend to reduce, for example, hernia mesh weight and stiffness as a means to reduce post operative complications and pain. A light weight mesh has a soft and pliant nature which conforms and flexes with movement of tissue. However, the reduction of mesh weight may make it hard to use, handle, and unfold the mesh during implantation, especially in a wet environment. A common complaint of surgeons is the inability to easily place a mesh and correctly position it prior to tacking, due to the mesh folding upon itself, gripping itself, and/or falling down due to gravity.

Improved meshes and methods for their application thus remain desirable.

SUMMARY

The present disclosure provides compositions suitable for adhering medical devices, such as meshes, to tissue, and methods for their preparation and use.

In embodiments, a method of the present disclosure includes applying a sprayable material to tissue, the sprayable material including at least one functional group capable of binding to tissue and at least one nucleotide; allowing the at least one functional group on the sprayable material to bind to the tissue; applying an implant to the sprayable material, the implant possessing at least a second nucleotide complementary to the at least one nucleotide; and permitting the at least one nucleotide on the sprayable material to bond with the second nucleotide on the implant, thereby binding the implant to the sprayable material.

In embodiments, the medical device, such as a mesh, may possess a surface feature such as dimples, grains, grooves, folds, textures, wrinkles, and combinations thereof, that are introduced into the device during its formation, prior to cooling the polymeric material utilized to form the device below its glass transition temperature. The device may then be heated to a temperature above the glass transition temperature of the polymeric material utilized to form the device after applying the implant to the sprayable material. Heat may be provided by the body itself, or some other suitable external source of heat. The material used to fabricate the device, sometimes referred to as a biomaterial, softens and becomes smoother, allowing for more surface contact between the implant and the sprayable material on the tissue, so that the nucleotides on the surface of the implant come into full contact with the free nucleotides on the sprayable material, thereby bonding thereto by hydrogen bonding.

DETAILED DESCRIPTION

Figure 1:
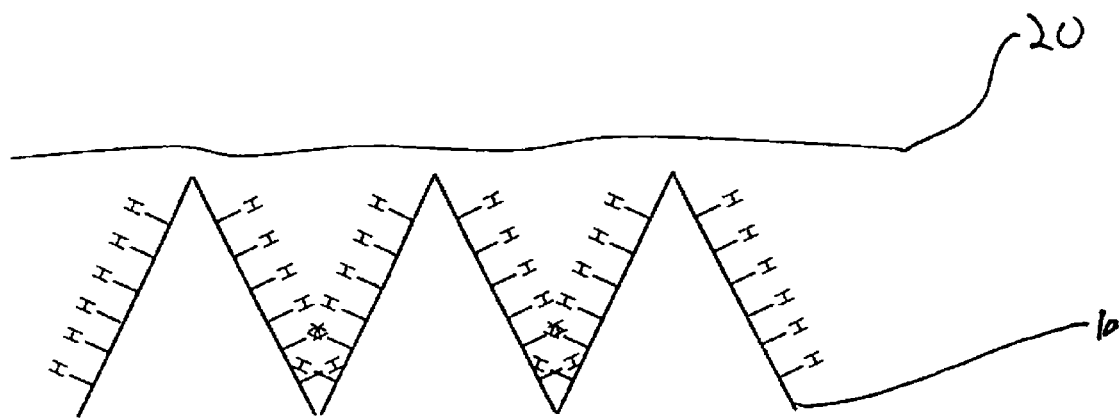
FIG. 1 illustrates a mesh of the present disclosure, prior to application to tissue.

In accordance with the present disclosure, a sprayable material is provided which facilitates the attachment of an implant, in embodiments a surgical mesh, to tissue. The sprayable material permits the temporary attachment of the mesh to tissue, which permits for better control during the placement of the mesh or other film/biomaterial, and provides one with the ability to adjust and/or reposition the mesh prior to attaching the mesh with more permanent means, such as a staple, tack, clip, suture, combinations thereof, and the like.

In accordance with the present disclosure, the sprayable material includes a component capable of binding tissue at one part, that is also capable of binding an implant at another part. Thus, in accordance with the present disclosure, the sprayable material of the present disclosure may have at least one functional group capable of binding to tissue, and at least one functional group capable of binding to an implant, such as a mesh or some other similar film or biomaterial. The functional group capable of binding to tissue and implant may be the same or different, depending upon the material utilized to form the implant. The term "functional group" as used herein refers to groups capable of reacting with tissue to form a bond, or capable of reacting with another group contained on an implant or mesh, thereby binding to the implant or mesh.

In accordance with the present disclosure, the component useful for forming the sprayable material may have biologically inert and water soluble cores, as well as non-water soluble cores. When the core is a polymeric region that is water soluble, suitable polymers that may be used include: polyethers, for example, polyalkylene oxides such as polyethylene glycol ("PEG"), polyethylene oxide ("PEO"), polypropylene oxide ("PPO"), polyethylene oxide-co-polypropylene oxide ("PEO-PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, hydroxymethylcellulose; hyaluronic acid; and proteins such as albumin, collagen, casein, and gelatin. In embodiments, combinations of the foregoing polymers may be utilized.

The polyethers, and more particularly poly(oxyalkylenes) or poly(ethylene glycol) or polyethylene glycol, may be utilized in some embodiments. When the core is small in molecular nature, any of a variety of hydrophilic functionalities can be used to make the sprayable material water soluble. For example, functional groups like hydroxyl, amine, sulfonate and carboxylate, which are water soluble, may be used to make the core water soluble. For example, the n-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

As noted above, the component useful for forming the sprayable material of the present disclosure is multifunctional, meaning that it has both functional groups capable of binding to tissue as well as additional functional groups capable of binding to an implant, such as a mesh.

The core of the sprayable material may be divalent, i.e., with a tissue reacting functional group on one end and a functional group capable of binding to an implant on the other end. As noted above, the functional group capable of reacting with tissue may be the same or different as the functional group capable of reacting with the implant, depending upon the material utilized to form the implant.

In embodiments, the core may include both natural and synthetic biodegradable materials, as well as combinations thereof.

Representative natural biodegradable macromolecules include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups include, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, soybean protein, and copolymers and blends thereof; alone or in combination with synthetic polymers.

Representative synthetic biodegradable macromolecules which may be utilized include polyhydroxy acids prepared from lactone monomers such as glycolide, lactide, caprolactone, ε-caprolactone, valerolactone, and δ-valerolactone; carbonates (e.g., trimethylene carbonate, tetramethylene carbonate, and the like); dioxanones (e.g., 1,4-dioxanone and p-dioxanone); 1,dioxepanones (e.g., 1,4-dioxepan-2-one and 1,5-dioxepan-2-one); and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactic-co-glycolic acid); poly(lactide-co-(ε-caprolactone-)); poly(glycolide-co-(ε-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; polyortho esters; and copolymers, block copolymers, homopolymers, blends, and combinations thereof.

The macromolecules may be functionalized to provide reactive sites. These reactive sites may themselves be capable of reacting with tissue and/or a substrate used to form an implant, or the reactive sites may be able to react with an additional end group capable of reacting with tissue and/or a substrate used to form an implant. For example, amines may be provided on proteins, aminoglycans (such as chitosan, chondrotins, hyaluronic acid, and heparin), and polypeptides (like polylysine); carboxyl groups may be provided on proteins, polypeptides (like poly(glutamic acid)), polysaccharides (such as carboxylated dextran and carboxymethyl cellulose), and synthetic polymers (like carboxylated PEG and PEG-diadipate); hydroxyl groups may be provided on polysaccharides (like dextran), di-PEG adipate, and aliphatic polyesters (such as poly(lactic acid), poly(glycolic acid), poly(caprolactone), poly(trimethylene carbonate, poly(P-Dioxanone), and copolymers thereof); and thiols may be provided on some proteins. Alternatively, the core may be functionalized with tissue or substrate binding end groups, such as poly(lactic acid) and/or poly(glycolic acid), which include terminal carboxyl or hydroxyl groups.

In embodiments, the core of the sprayable material may be multi-armed. For example, the core of the sprayable material may be a multi-armed PEG having four, six, eight, or more arms extending from a core. The core may be the same or different from the macromolecule forming the arms. For example, the core may be PEG and the multiple arms may also be PEG. In embodiments, the core may be a natural polymer.

The molecular weight (MW) of the core of the sprayable material may be from about 800 to about 100,000; in embodiments from about 4,000 to about 40,000. Multi-arm precursors may have a molecular weight that varies depending on the number of arms. For example, an arm having a 1000 MW of PEG has enough $CH_2CH_2O$ groups to total at least 1000 MW. The combined molecular weight of an individual arm may be from about 100 to about 5,000; in embodiments from about 250 to about 2,500; in embodiments from about 350 to about 1,000.

As noted above, the core utilized to form the sprayable material of the present disclosure possesses functional groups capable of binding to tissue, as well as functional groups capable of binding to an implant. The functional group capable of binding to tissue may bind to amines, carboxyl groups, hydroxyl groups, or any other chemistry present on the tissue surface to which the implant is to be attached. Such groups include, for example, isocyanates, N-hydroxy succinimides ("NHS"), cyanoacrylates, aldehydes (e.g., formaldehydes, glutaraldehydes, glyceraldehydes, and dialdehydes), and other compounds possessing chemistries having some affinity for tissue, as well as combinations thereof.

As noted above, in embodiments, the tissue or substrate binding end group may be conjugated to the core through the use of a linking agent. For amine containing macromolecules, for example, isothiocyanates, isocyanates, acyl azides, N-hydroxysuccinimide (NHS) and sulfo-NHS esters, sulfonyl chlorides, aldehydes and glyoxals, epoxides and oxiranes, carbonates, arylating agents, imidoesters, carbodiimides, and anhydrides may be utilized. For carboxyl containing macromolecules, for example, diazoalkanes and diazoacetyl compounds may be utilized, as well as carbonyldiimidazoles, carbodiimides, and NHS, which convert carboxylic acid into a reactive intermediate which is susceptible to reaction with amines or alcohols. For hydroxyl containing macromolecules, for example, epoxides and oxiranes, acyl azides, carbonyldiimidazole, disuccinimidyl carbonate and hydroxysuccinimidyl chloroformate, alkyl halogens, isocyanates, and methacryloyl or acryloyl chloride may be utilized, as well as oxidation with periodate and enzymatic oxidation.

In some embodiments, the tissue or substrate binding end groups may be conjugated to the core via succinimidyl esters such as NHS and sulfo-NHS; isocyanates and isothiocyanates; aldehydes such as oxidized starch, oxidized dextran, and oxidized PEG; and by Michael's Addition of acrylates which react with thiol groups.

As noted above, the sprayable material may also possess a functional group which is capable of binding to an implant. In embodiments, the binding of the sprayable material to an implant may occur by hydrogen bonding. Thus, in accordance with the present disclosure, both the sprayable material and an implant may possess groups capable of hydrogen bonding, so that a functional group on the sprayable material hydrogen bonds with a functional group on the implant. For example, in embodiments, the functional groups on the sprayable material and/or implants, which may be attached to the implant, sprayable material, or both using linking agents described above, may be nucleotides, including cytosine, guanine, adenine, thymine, uracil, combinations thereof, and the like. In this case, an implant of the present disclosure may possess a complementary nucleotide to the nucleotide found on the sprayable material, thus permitting hydrogen bonding between the two. For example, cytosine forms a base pair with guanine through hydrogen bonding, and adenine forms a base pair with thymine and/or uracil through hydrogen bonding. Thus, by selecting nucleotides on the sprayable material that are complementary to the nucleotides found on the implant, one can tailor a sprayable material/implant combination that will permit the temporary attachment of the implant to tissue through hydrogen bonding.

While the above disclosure has focused on the hydrogen bonding of an implant of the present disclosure, such as a mesh, with the sprayable material, it is contemplated that other complementary binding mechanisms may be utilized. For example, either the sprayable material or implant may include electrophilic or nucleophilic functional groups, such that, for example, a nucleophilic functional group on the sprayable material may react with an electrophilic functional group on the implant to form a covalent bond, or an electrophilic functional group on the sprayable material may react with a nucleophilic functional group on the implant to form a covalent bond.

Exemplary functional components, and methods for forming these functional components, include those disclosed in detail above, as well as those disclosed in, for example, U.S. Pat. Nos. 7,347,850, 7,332,566, 7,009,034, and 6,566,406, the entire disclosures of each of which are incorporated by reference herein.

As described above, the sprayable material of the present disclosure is applied to tissue prior to application of an implant thereto. Thus, the sprayable material should be in a form which permits spraying. Suitable sprayable materials include, for example, powders, solutions, combinations thereof, and the like.

In embodiments the sprayable material may be in a solution. Suitable solvents for forming such solutions include, but are not limited to, water; saline; buffer salts; alcohols including methanol, ethanol, and propanol; dimethyl sulfoxide; dimethylformamide; chlorinated hydrocarbons such as methylene chloride, chloroform, and 1,2-dichloro-ethane; aliphatic hydrocarbons such as hexane, heptene, and ethyl acetate; combinations thereof, and the like.

Where the sprayable material is a solution, the component possessing the functional groups capable of binding to tissue and an implant may be present in the solution at a concentration of from about 1% to about 100% by weight of the solution, in embodiments from about 20% to about 90% by weight of the solution.

Applicators for applying the sprayable materials include powder sprayers, syringes, droppers, markers or pen-like applicators, brushes, sponges, patches, combinations thereof, and the like.

After applying the sprayable materials onto tissue, the functional groups capable of binding to tissue may form covalent bonds to tissue within about 60 seconds after spraying, in embodiments from about 3 second to about 15 seconds after spraying, after which an implant may be applied to the area that has been sprayed. As noted above, in embodiments, the implant may possess groups, in embodiments nucleotides, capable of hydrogen bonding with the nucleotides on the sprayable material.

In embodiments, the sprayable materials of the present disclosure may also include visualization agents, such as a dye. Suitable dyes are within the purview of those skilled in the art and may include, for example, a dye for visualizing a thickness of the hydrogel as it is formed in situ, e.g., as described in U.S. Pat. No. 7,009,034, the entire disclosure of which is incorporated by reference herein. In some embodiments, a suitable dye may include FD&C Blue No. 1, FD&C Blue No. 2, FD&C Blue No. 3, D&C Green No. 6, methylene blue, combinations thereof, and the like.

The hydrogen bonding of the sprayable material to the implant thus permits temporary attachment of the implant to tissue, allowing for the controlled placement of the implant, as well as the ability to adjust and/or reposition the implant, prior to final tacking/fixing of the implant to tissue.

Implants of the present disclosure may be of any type suitable for use within the body. In embodiments, an implant may be a surgical mesh or similar film. The surgical meshes are suitable for surgical repair of hernias and other surgical procedures requiring reinforcement or repair of soft tissue, such as muscle or wall tissue defects, pelvic organ prolapse, and urinary incontinence, for example. The meshes of the present disclosure can be in the form of sheets, patches, slings, suspenders, and other implants and composite materials such as pledgets, buttresses, wound dressings, drug delivery devices, and the like. The present surgical meshes may be implanted using open surgery or by a laparoscopic procedure.

A surgical mesh in accordance with the present disclosure may be fabricated from monofilament and/or multifilament yarns which may be made of any suitable biocompatible material. Suitable materials from which the mesh can be made should have the following characteristics: sufficient tensile strength to support tissue; sufficiently inert to avoid foreign body reactions when retained in the body for long periods of time; easily sterilized to prevent the introduction of infection when the mesh is implanted in the body; and sufficiently strong to avoid tearing of portions thereof, including any portion through which surgical fasteners may be applied to affix the mesh to tissue.

In some embodiments, the yarns include at least two filaments which may be arranged to create openings therebetween, the yarns also being arranged relative to each other to form openings in the mesh. Alternatively, the mesh may be formed from a continuous yarn that is arranged in loops that give rise to the openings in the mesh. The use of a mesh having yarns spaced apart in accordance with the present disclosure has the advantage of reducing the foreign body mass that is implanted in the body, while maintaining sufficient tensile strength to securely support the defect and tissue being repaired by the mesh. Moreover, the openings of the mesh of the present disclosure may be sized to permit fibroblast through-growth and ordered collagen laydown, resulting in integration of the mesh into the body. Thus, the spacing between the yarns may vary depending on the surgical application and desired implant characteristics as envisioned by those skilled in the art. Moreover, due to the variety of sizes of defects, and of the various fascia that may need repair, the mesh may be of any suitable size.

In embodiments in which at least two filaments form a yarn, the filaments may be drawn, oriented, crinkled, twisted, braided, commingled or air entangled to form the yarn. The resulting yarns may be braided, twisted, aligned, fused, or otherwise joined to form a variety of different mesh shapes. The yarns may be woven, knitted, interlaced, braided, or formed into a surgical mesh by non-woven techniques. The structure of the mesh will vary depending upon the assembling technique utilized to form the mesh, as well as other factors, such as the type of fibers used, the tension at which the yarns are held, and the mechanical properties required of the mesh.

In embodiments, knitting may be utilized to form a mesh of the present disclosure. Knitting involves, in embodiments, the intermeshing of yarns to form loops or inter-looping of the yarns. In embodiments, yarns may be warp-knitted thereby creating vertical interlocking loop chains, and/or yarns may be weft-knitted thereby creating rows of interlocking loop stitches across the mesh. In other embodiments, weaving may be utilized to form a mesh of the present disclosure. Weaving may include, in embodiments, the intersection of two sets of straight yarns, warp and weft, which cross and interweave at right angles to each other, or the interlacing of two yarns at right angles to each other. In some embodiments, the yarns may be arranged to form a net mesh which has isotropic or near isotropic tensile strength and elasticity.

In embodiments, the yarns may be nonwoven and formed by mechanically chemically or thermally bonding the yarns into a sheet or web in a random or systematic arrangement. For example, yarns may be mechanically bound by entangling the yarns to form the mesh by means other than knitting or weaving, such as matting, pressing, stitch-bonding, needlepunching, or otherwise interlocking the yarns to form a binderless network. In other embodiments, the yarns of the mesh may be chemically bound by use of an adhesive such as a hot melt adhesive, or thermally bound by applying a binder such as a powder, paste, or melt, and melting the binder on the sheet or web of yarns.

The yarns may be fabricated from any biodegradable and/or non-biodegradable polymer that can be used in surgical procedures. The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body, such that the degradation products are excretable or absorbable by the body. Absorbable materials are absorbed by biological tissues and disappear in vivo at the end of a given period, which can vary, for example, from hours to several months, depending on the chemical nature of the material. It should be understood that such materials include natural, synthetic, bioabsorbable, and/or certain non-absorbable materials, as well as combinations thereof.

Representative natural biodegradable polymers which may be used to form the yarns include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups including, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, soybean protein; and combinations such as copolymers and blends thereof, alone or in combination with synthetic polymers.

Synthetically modified natural polymers which may be used to form the yarns include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and combinations thereof.

Representative synthetic biodegradable polymers which may be utilized to form yarns include polyhydroxy acids prepared from lactone monomers (such as glycolide, lactide, caprolactone, ε-caprolactone, valerolactone, and δ-valerolactone), carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; polyortho esters; and copolymers, block copolymers, homopolymers, blends, and combinations thereof.

Synthetic degradable polymers also include hydrophilic vinyl polymers expanded to include phosphoryl choline such as 2-methacryloyloxyethyl phosphorylcholine, hydroxamates, vinyl furanones and their copolymers, and quaternary ammonia; as well as various alkylene oxide copolymers in combination with other polymers such as lactones, orthoesters, and hydroxybutyrates, for example.

Rapidly bioerodible polymers, such as poly(lactide-co-glycolide)s, polyanhydrides, and polyorthoesters, which have carboxylic groups exposed on the external surface as the surface of the polymer erodes, may also be used.

Other biodegradable polymers include polyphosphazenes; polypropylene fumarates; polyimides; polymer drugs such as polyamines; perfluoroalkoxy polymers; fluorinated ethylene/propylene copolymers; PEG-lactone copolymers; PEG-polyorthoester copolymers; blends and combinations thereof.

Some non-limiting examples of suitable nondegradable materials from which the mesh may be made include polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoropolyethylene glycols, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

The mesh may be a composite of layers, including a fibrous layer as described above, as well as porous and/or non-porous layers of fibers, foams, and/or films. A non-porous layer may retard or prevent tissue ingrowth from surrounding tissues, thereby acting as an adhesion barrier and preventing the formation of unwanted scar tissue. In embodiments, a reinforcement member may be included in the composite mesh. Suitable meshes, for example, include a collagen composite mesh such as PARIETEX™ (Tyco Healthcare Group LP, d/b/a Covidien, North Haven, Conn.). PARIETEX™ composite mesh is a 3-dimensional polyester weave with a resorbable collagen film bonded on one side. Examples of other meshes which may be utilized include those disclosed in U.S. Pat. Nos. 6,596,002; 6,408,656; 7,021,086; 6,971,252; 6,695,855; 6,451,032; 6,443,964; 6,478,727; 6,391,060; and U.S. Patent Application Publication No. 2007/0032805, the entire disclosures of each of which are incorporated by reference herein.

Surgical meshes in accordance with the present disclosure are fabricated from a textile which provides the primary structure to the implants. As noted above, the implants possess functional groups which may be nucleotides. These functional groups may be introduced onto the surface of an implant using means within the purview of one skilled in the art, including any of those described above as suitable for introducing a functional group on the core.

Figure 2:
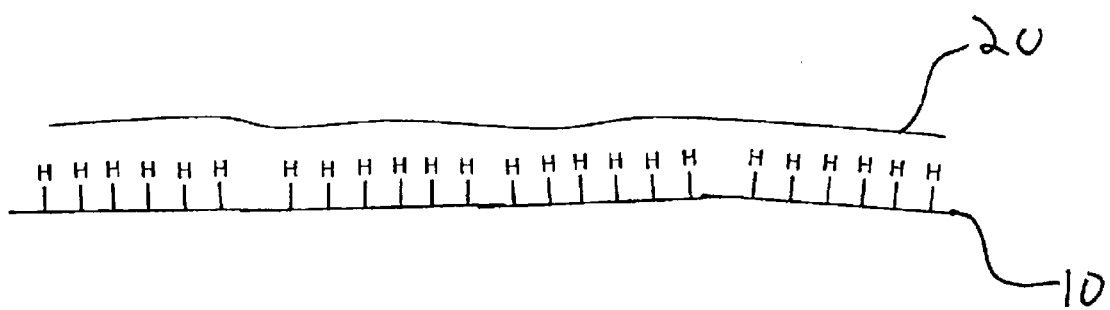
FIG. 2 illustrates a mesh of the present disclosure after application to tissue.

In embodiments, the surgical mesh may include a polymeric material having a glass transition temperature from about 40° C. to about 60° C., and a surface that has been modified to include nucleotides capable of complementary hydrogen bonding with nucleotides or similar materials present in the sprayable material. As depicted in FIG. 1, when the implant 10 is in the body, it will be at a temperature below its glass transition temperature (Tg) and will not readily bond to the sprayable material on tissue 20, as the surface of the implant will be rough and have limited contact with the complementary nucleotides on the sprayable material. However, as depicted in FIG. 2, when locally heated to a temperature above the Tg of the polymer utilized to form the implant, the implant 10 will soften and conform to the tissue 20, thereby allowing for more surface contact between the implant 10 and sprayable material on tissue 20, and thus permitting hydrogen bonding between the nucleotides on the implant and sprayable material. Suitable heat sources include the application of heated fluids such as hot air, warm saline, combinations thereof, and the like. Other suitable heat sources include, for example, sources of radiation including visible light, infrared radiation, combinations thereof, and the like. In this manner, the implant may thus be affixed to tissue. If the surgeon wanted to undo the tack, heat could be locally applied and the mesh could be pulled loose. Additional heating and again contacting the implant with the sprayable material would thus permit reformation of hydrogen bonds between the nucleotides on the implant and sprayable material, thus allowing the implant to once again become tacked to tissue.

In other embodiments, the surgical meshes may include a polymeric material having a glass transition temperature between room and body temperature, in embodiments from about 25° C. to about 37° C., in other embodiments from about 30° C. to about 35° C. For such a material, the polymeric material may be heated to a temperature above its glass transition temperature, and a surface feature, including dimples, grains, grooves, folds, textures, wrinkles, combinations thereof, and the like, may be mechanically introduced to the otherwise smooth polymeric material. The temperature may then be quickly lowered below the glass transition temperature of the polymeric material, thereby locking the surface feature into the material. When the implant is then placed into the body, its adherent functional groups capable of forming hydrogen bonds, in embodiments nucleotides, on the roughened surface would not adhere to the sprayable material as the surface area of contact on the biomaterial would be minimal. However, as the material is warmed to body temperature, which is above its glass transition temperature, the biomaterial softens and once again becomes smoother, allowing for more surface contact between the implant and the sprayable material on the tissue, so that the nucleotides on the surface of the implant would be able to come into full contact with the free nucleotides on the sprayable material, thereby bonding thereto by hydrogen bonding.

In other embodiments, a shape memory material may be used to form an implant of the present disclosure. The glass transition temperature of such a shape memory material may be from about 40° C. to about 60° C., in other embodiments from about 45° C. to about 55° C. Similar to the embodiments described above, the implant may be heated to a temperature above its glass transition temperature and a surface feature applied thereto as described above, and then the material may be cooled to a temperature below its glass transition temperature, thereby locking the surface feature into the material. Once implanted in the body, the shape memory material may be locally heated by a suitable heat source, including the application of heated fluids such as hot air, warm saline, combinations thereof, and the like. Other suitable heat sources include, for example, sources of radiation including visible light, infrared radiation, combinations thereof, and the like. The heat source heats the shape memory material to a temperature above its glass transition temperature, at which time the material softens and becomes smoother, allowing for more surface contact between the implant and the sprayable material on the tissue, so that the nucleotides on the surface of the implant would be able to come into full contact with the free nucleotides on the sprayable material, thereby bonding thereto by hydrogen bonding.

In embodiments, at least one side of the surgical mesh may be covered with functional groups permitting hydrogen bonding. In yet other embodiments, the entire surgical mesh is covered with these functional groups. The coating may cover from about 10% to about 100% of the area of the mesh, in embodiments from about 30% to about 75% of the area of the mesh. In embodiments, the coating may cover selected areas of the mesh, such as the perimeter. In other embodiments the coating may be applied to intermittent areas of the mesh in lines, rows, patterns, concentric shapes, combinations thereof, and the like. The amount of coating may also be by weight percent of the coated mesh, i.e., the coating may be present in an amount of from about 0.1% to about 20% by weight of the total weight of the mesh, in embodiments, from about 1% to about 10% by weight of the total weight of the mesh.

Thus, for example, in embodiments, a suitable sprayable material may possess a nucleotide on one end, and NHS on the other end, solubilized at a high concentration in a slightly basic buffer, and sprayed onto desired tissue. The NHS reacts with amines on the tissue, thereby creating a surface having a high amount of the nucleotide. A mesh that has been surface modified with a complementary nucleotide may then be applied thereto, and heat may be applied, so that the mesh conforms to the tissue surface and hydrogen bonding occurs between the nucleotides on the mesh and the previously applied sprayable material. The mesh may be repositioned as necessary, after which time a more permanent means of fixation, such as a staple, clip, suture, screw, or some other fastener, may be applied to the mesh to affix it to the tissue.

Bioactive agents may be added to the sprayable material and/or a surgical mesh of the present disclosure. A "bioactive agent", as used herein, is used in its broadest sense and includes any substance or mixture of substances that have clinical use. Consequently, bioactive agents may or may not have pharmacological activity per se, e.g., a dye. Alternatively, a bioactive agent could be any agent which provides a therapeutic or prophylactic effect; a compound that affects or participates in tissue growth, cell growth and/or cell differentiation; a compound that may be able to invoke or prevent a biological action such as an immune response; or a compound that could play any other role in one or more biological processes. A variety of bioactive agents may be incorporated into the mesh. Moreover, any agent which may enhance tissue repair, limit the risk of sepsis, and modulate the mechanical properties of the mesh (e.g., the swelling rate in water, tensile strength, etc.) may be added during the preparation of the surgical mesh or may be coated on or into the openings of the mesh. The bioactive agent may be applied to the individual fibers of the surgical mesh or may be applied to the formed surgical mesh, or just one or more sides or portions thereof. In embodiments, the bioactive agent may be added to the polymeric coating.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Other bioactive agents which may be in the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present disclosure include: small molecule drugs; viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons ($\beta$-IFN, ($\alpha$-IFN and $\gamma$-IFN)); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists; protein agonists; nucleic acids such as antisense molecules, DNA, and RNA; oligonucleotides; and ribozymes.

It will be understood that various modifications may be made to the embodiments disclosed herein. Therefore, the above description should not be construed as limiting, but merely as an exemplification of illustrative embodiments. Those skilled in the art will envision other modifications within the scope and spirit of the present disclosure. Such modifications and variations are intended to come within the scope of the following claims.

What is claimed is:

1. A method for attaching an implant to a tissue comprising:
   applying a sprayable material to a tissue, the sprayable material comprising at least one functional group capable of attaching said sprayable material to the tissue and further comprising at least one first nucleotide;
   allowing the at least one functional group on the sprayable material to attach to the tissue;

applying to the sprayable material an implant having a surface possessing at least one second nucleotide complementary to the at least one first nucleotide on the sprayable material, wherein the sprayable material comprises a multi-arm polyethylene glycol and the sprayable material is not the implant; and permitting the at least one first nucleotide on the sprayable material to bond with the second nucleotide on the surface of the implant so as to allow the implant to bind to the sprayable material, thereby attaching the implant to the target tissue.

2. The method of claim 1, wherein the sprayable material comprises a core selected from the group consisting of polyalkylene oxides, polyvinyl alcohol, poly(vinyl pyrrolidinone), poly(amino acids), poly(saccharides), hyaluronic acid, proteins, and combinations thereof.

3. The method of claim 1, wherein the at least one functional group capable of binding to tissue is selected from the group consisting of isocyanates, N-hydroxy succinimides, cyanoacrylates, aldehydes, and combinations thereof.

4. The method of claim 1, wherein the nucleotides on the sprayable material and the implant are selected from the group consisting of cytosine, guanine, adenine, thymine, uracil, and combinations thereof.

5. The method of claim 1, wherein the implant comprises a mesh.

6. The method of claim 5, wherein the mesh comprises a polymeric material having a glass transition temperature from about 40° C. to about 60° C.

7. The method of claim 6, wherein the mesh possesses a surface feature selected from the group consisting of dimples, grains, grooves, folds, textures, wrinkles, and combinations thereof, that are introduced into the mesh prior to cooling the polymeric material below its glass transition temperature.

8. The method of claim 6, further comprising heating the mesh to a temperature above the glass transition temperature of the polymeric material after applying the implant to the sprayable material.

9. The method of claim 5, wherein the mesh comprises a polymeric material having a glass transition temperature from about 25° C. to about 37° C.

10. The method of claim 9, wherein the mesh possesses a surface feature selected from the group consisting of dimples, grains, grooves, folds, textures, wrinkles, and combinations thereof, that are introduced into the mesh prior to cooling the polymeric material below its glass transition temperature.

11. The method of claim 10, wherein the introduction of the mesh into the body warms the mesh to a temperature above its glass transition temperature, so that the polymeric material softens and becomes smoother.

12. The method of claim 5, wherein the mesh comprises a shape memory material having a glass transition temperature from about 40° C. to about 60° C.

13. The method of claim 12, wherein the mesh possesses a surface feature selected from the group consisting of dimples, grains, grooves, folds, textures, wrinkles, and combinations thereof, that are introduced into the mesh prior to cooling the polymeric material below its glass transition temperature.

14. The method of claim 12, further comprising heating the implant in the body to a temperature above its glass transition temperature, at which point the material softens and becomes smooth.

15. The method of claim 5, wherein at least one side of the mesh may be covered with functional groups permitting hydrogen bonding.

16. The method of claim 5, wherein the functional groups comprise a coating on the mesh present in an amount from about 10% to about 100% of the area of the mesh.

17. The method of claim 5, wherein the functional groups comprise a coating in an amount of from about 0.1% to about 20% by weight of the total weight of the mesh.

18. The method of claim 1, wherein the implant further comprises a bioactive agent.

* * * * *